(12) United States Patent
Tsukada et al.

(10) Patent No.: US 9,128,071 B2
(45) Date of Patent: Sep. 8, 2015

(54) LIQUID MIXING DEVICE AND LIQUID CHROMATOGRAPH

(75) Inventors: Nobuhiro Tsukada, Hitachinaka (JP); Yoshihiro Nagaoka, Ushiku (JP); Hironori Kaji, Hitachinaka (JP); Daisuke Akieda, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 353 days.

(21) Appl. No.: 13/704,247

(22) PCT Filed: May 18, 2011

(86) PCT No.: PCT/JP2011/002749
§ 371 (c)(1), (2), (4) Date: Dec. 14, 2012

(87) PCT Pub. No.: WO2011/158430
PCT Pub. Date: Dec. 22, 2011

(65) Prior Publication Data
US 2013/0091933 A1    Apr. 18, 2013

(30) Foreign Application Priority Data
Jun. 16, 2010  (JP) .................. 2010-136714

(51) Int. Cl.
*G01N 30/02* (2006.01)
*B01F 5/06* (2006.01)
*G01N 30/34* (2006.01)

(52) U.S. Cl.
CPC .............. *G01N 30/02* (2013.01); *B01F 5/0646* (2013.01); *G01N 30/34* (2013.01)

(58) Field of Classification Search
CPC ....... B01F 5/0646; G01N 30/02; G01N 30/34

USPC .......................................... 73/61.55; 366/339
See application file for complete search history.

(56) References Cited

U.S. PATENT DOCUMENTS

| 2009/0257920 | A1* | 10/2009 | Facer et al. | ............. 422/99 |
| 2010/0107742 | A1* | 5/2010 | Liu et al. | ............. 73/61.56 |
| 2011/0128814 | A1* | 6/2011 | Hanada | ............. 366/339 |

FOREIGN PATENT DOCUMENTS

| EP | 1788388 A1 | 5/2007 |
| JP | 62-95727 | 6/1987 |

(Continued)

OTHER PUBLICATIONS

Chinese Office Action of Appln. No. 201180029186.8 dated Jun. 26, 2014 with English translation.

*Primary Examiner* — Hezron E Williams
*Assistant Examiner* — David Z Huang
(74) *Attorney, Agent, or Firm* — Baker Botts L.L.P.

(57) ABSTRACT

A liquid mixing device that decreases a concentration non-uniformity in the flow direction of a mobile phase and a liquid chromatograph that uses the liquid mixing device are provided. The liquid mixing device is configured to include a flow channel unit that is made from an introduction channel, a branch portion that is positioned in a downstream of the introduction channel, multiple branched flow channels that branch from the branch portion, a junction portion in which the multiple branched flow channels join together, and a discharge channel of the downstream of the junction portion. The multiple branched flow channels are different in terms of any one of, or several of width, depth, and length that are associated with an external shape, and a structure filling the inside of the flow channel and thus the times for the liquid to pass through the branched flow channels are different from each other.

9 Claims, 10 Drawing Sheets

(56) References Cited

FOREIGN PATENT DOCUMENTS

| JP | 2004-351245 | 12/2004 |
| JP | 2007-139782 | 6/2007 |
| JP | 2008-221208 | 9/2008 |
| JP | 2008-264640 | 11/2008 |
| WO | WO 00/72001 | 11/2000 |
| WO | WO 2010/016448 A1 | 2/2010 |

* cited by examiner

LIQUID MIXING DEVICE AND LIQUID CHROMATOGRAPH

TECHNICAL FIELD

The present invention relates to a liquid mixing device that mixes a liquid, and a liquid chromatograph that uses the liquid mixing device.

BACKGROUND ART

A liquid mixing device for mixing multiple eluents into a mobile phase is used in a gradient elution method in a liquid chromatograph. The liquid mixing device is hereinafter referred to as a mixer. There are a mixer with a structure that is filled with beads in the form of small particles and a mixer with a structure in which a hole and a groove are formed on a substrate to serve as a flow channel. Among these, since the mixer with the structure that uses the flow channel may mix eluents using a small flow channel volume, the mixture time is short and the analysis time is short.

The structure is disclosed in PTL 1, which changes the cross-sectional shape of a branched flow channel at a branch point and at a junction point, in terms of the structure of the flow channel that facilitates the mixing using the branch and the junction of the flow channel. According to this structure, since the direction in which the liquid flowing through the flow channel branches and the direction in which the liquid flowing through the flow channel joins together change and an interface area of two liquids increases every branch and junction, a mixture effect is facilitated.

The method is disclosed in PTL 2, in which a specific change in concentration is caused in a gradient elution method mobile phase by the multiple flow channels through which the times for the liquid to pass are different and by a combination of the liquid sending timings of a liquid sending pump.

Citation List

Patent Literature

PTL 1: JP-A-2008-221208
PTL 2: JP-A-2007-139782

SUMMARY OF INVENTION

Technical Problem

In a liquid chromatograph, a concentration non-uniformity in the flow direction with respect to the flow channel occurs in the mobile phase immediately after the eluents join together. This is because in the configuration of a high pressure gradient elution method, a liquid sending pump has a pulsation in the amount of the flowing liquid that results from, for example, the operation variations of a check valve. Furthermore, this is because in the configuration of a low pressure gradient elution method, a switch valve sequentially sends the multiple eluents into a pipe one kind of eluent at a time. The mixer that has the structure using the related flow channel serves the purpose of mixing in the width direction with respect to the flow channel, and thus the effect of mixing in the flow direction with respect to the flow channel is small. For this reason, the concentration non-uniformity in the flow direction remains in the mobile phase that flows into a detector. As a result, for example, in a case where the light absorbance measurement is used in the detector, a change corresponding to the extent of the concentration non-uniformity of the mobile phase occurs in the detected light absorbance.

An object of the present invention is to provide a liquid mixing device that decreases a concentration non-uniformity in the flow direction of a mobile phase, and a liquid chromatograph that uses the liquid mixing device.

Solution to Problem

According to an embodiment of the present invention, there is provided a liquid mixing device configured to include a flow channel unit that is made from an introduction channel, a branch portion that is positioned in a downstream of the introduction channel, multiple branched flow channels that branch from the branch portion, a junction portion in which the multiple branched flow channels join together, and a discharge channel of the downstream of the junction portion. The multiple branched flow channels are different in terms of any one of, or several of width, depth; and length that are associated with an external shape, and a structure filling the inside of the flow channel and thus the times for the liquid to pass through the branched flow channels are different from each other. Since the times for the liquid to pass through the branched flow channels are different from each other, concentrations of a mobile phase that passes through the branched flow channels are different in the junction portion from each other. As a result, the concentration of the mobile phase in the junction portion is between values of the concentrations of the mobile phase that passes through each branched flow channel. That is, the concentration non-uniformity in the flow direction of the mobile phase in the discharge channel is decreased more than the concentration non-uniformity in the flow direction of the mobile phase in the introduction channel.

When independently using the flow channel unit, with respect to a difference between the times for the liquid to pass through the branched flow channels, there is a period of the concentration non-uniformity in which the performance of decreasing the concentration non-uniformity in the flow direction of the mobile phase is at the maximum. Then, with the configuration of a liquid sending pump that may always send the liquid with a period of the concentration non-uniformity without depending on the amount of the flowing liquid, and the liquid chromatograph that uses the flow channel unit, the concentration non-uniformity in the flow direction may be remarkably decreased.

Furthermore, the multiple flow channel units are connected to each other in multiple stages in such a manner that the liquid passing through the junction portion in the upper-stage flow channel unit flows into the branch portion in the lower-stage flow channel unit. At this time, the differences between the times for the liquid to pass through the branched flow channels in the flow channel unit at each stage are different from each other. According to this configuration, since the periods of the concentration non-uniformity that is decreased in each flow channel unit are different, the concentration non-uniformity of the various periods may be decreased as a whole. Therefore, the concentration non-uniformity in the flow direction may be decreased, without depending on the pulsation period of the liquid sending pump.

Advantageous Effects of Invention

According to the embodiment of the present invention, there may be provided a liquid mixing device that decreases the concentration non-uniformity in the flow direction of the mobile phase and a liquid chromatograph that uses the liquid mixing device.

DESCRIPTION OF EMBODIMENTS

Figure 1:
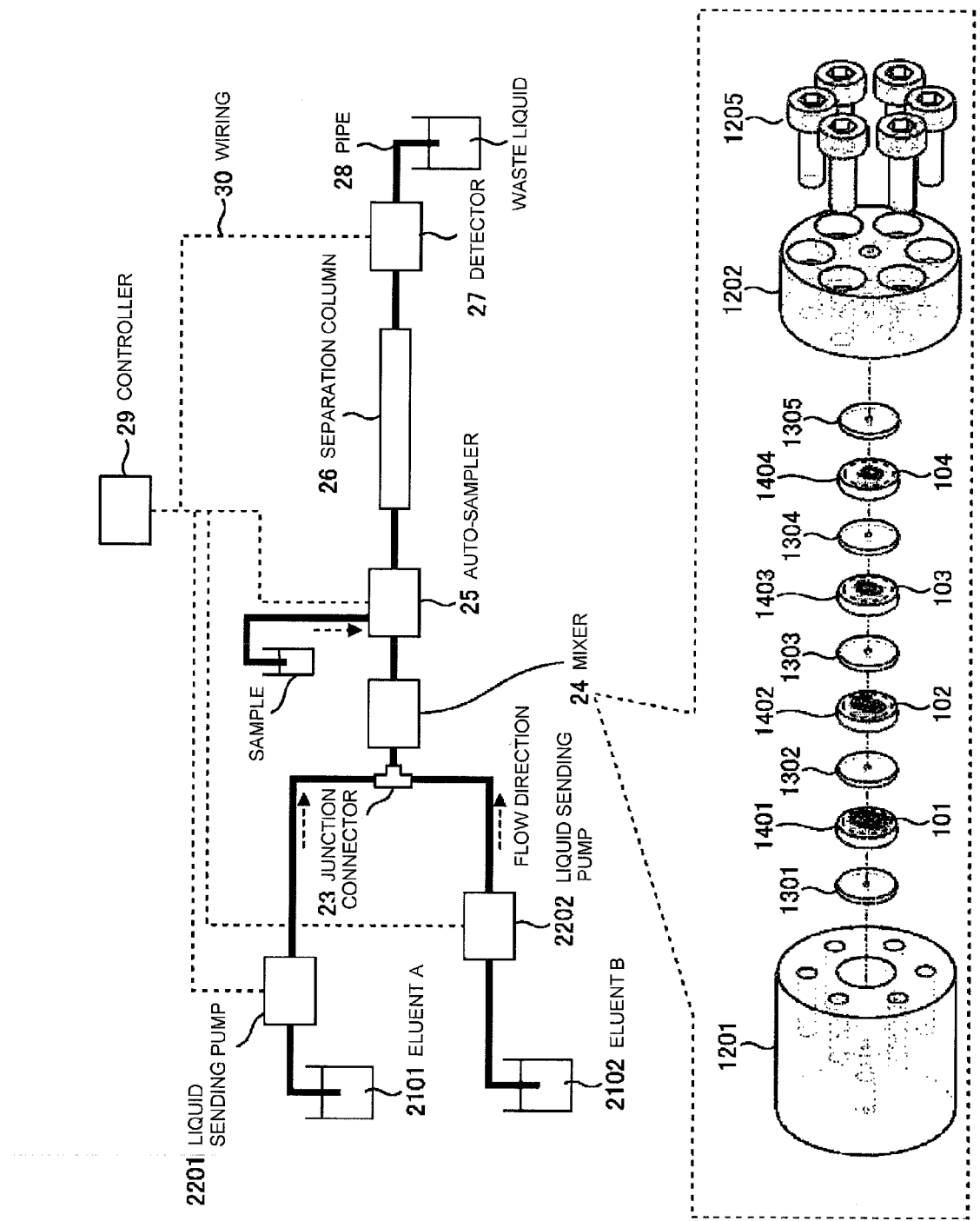
FIG. 1 is a configuration diagram illustrating a main configuration of a liquid chromatograph for a high pressure gradient elution method.

Examples of the present invention are described below referring to the drawings.

Example 1

FIG. 1 is a configuration diagram illustrating a main configuration of a liquid chromatograph for a high pressure gradient elution method. The liquid chromatograph illustrated in FIG. 1 includes two kinds of eluents 2101 and 2102, two liquid sending pumps 2201 and 2202, a junction connector 23, a mixer 24, an auto-sampler 25, a separation column 26, a detector 27, a pipe 28 that connects components to one another in a manner that enables the liquid to flow, a controller 29 that controls each component, and wiring 30 that electrically connects components one another.

The mixer 24 is made from a housing bottom 1201, a housing lid 1202, flow channel substrates 1401, 1402, 1403, and 1404, spacers 1301, 1302, 1303, 1304, and 1305 that are inserted between the flow channel substrates, between the flow channel substrate and the housing bottom 1201, or the flow channel substrate and the housing lid 1202, and screws 1205 that join these components to one another. A configuration in which the mixer has four of the flow channel substrates is illustrated in FIG. 1, but the number of the flow channel substrates is not necessarily limited to four.

As the material of the housing bottom 1201 and the housing lid 1202, for example, stainless steel and polyetheretherketone, are enumerated. Among these, in order to prevent liquid leakage from a connection portion with a pipe, it is desirable to connect the housing bottom and the housing lid that are made of stainless steel and the pipe that is made of stainless steel.

The spacers 1301, 1302, 1303, 1304, and 1305 have a function of providing sealing between the flow channel substrates, between the flow channel substrate and the housing bottom 1201, or between the flow channel substrate and the housing lid 1202. The surfaces adhere to each other and thus liquid is prevented from leaking out of the flow channel by joining the housing bottom 1201 and the housing lid 1202 with screws 1205. As the material of the spacers 1301, 1302, 1303, 1304, and 1305, for example, polyetheretherketone and polytetrafluoroethylene, which have low dissolution into a mobile phase and may seal each surface by being deformed to some extent at the time of joining together, are desirable. In a case where, for example, polyether ether ketone and polytetrafluoroethylene that have high deformability are selected as the material of the flow channel substrates 1401, 1402, 1403, and 1404, the spacers 1301, 1302, 1303, 1304, and 1305 are not necessarily required because the flow channel substrate 1401 and the housing bottom 1201, the flow channel substrate 1404 and the housing lid 1202, and the flow channel substrates 1401, 1402, 1403, and 1404 adhere to each other.

The flow channel unit is formed in the flow channel substrates 1401, 1402, 1403, and 1404. As the material of the flow channel substrates, for example, stainless steel, polyetheretherketone, polytetrafluoroethylene, silicon, glass, polydimethylsiloxane, and ultraviolet curing resin are enumerated. Among these, for example, stainless steel, polyetheretherketone, and polytetrafluoroethylene are advantageous in that the dissolution into the eluent is low. As a method of processing the flow channel unit into the flow channel substrate, for example, machining, wet etching, dry etching, hot embossing, injection molding, and photofabrication are enumerated.

Figure 2:
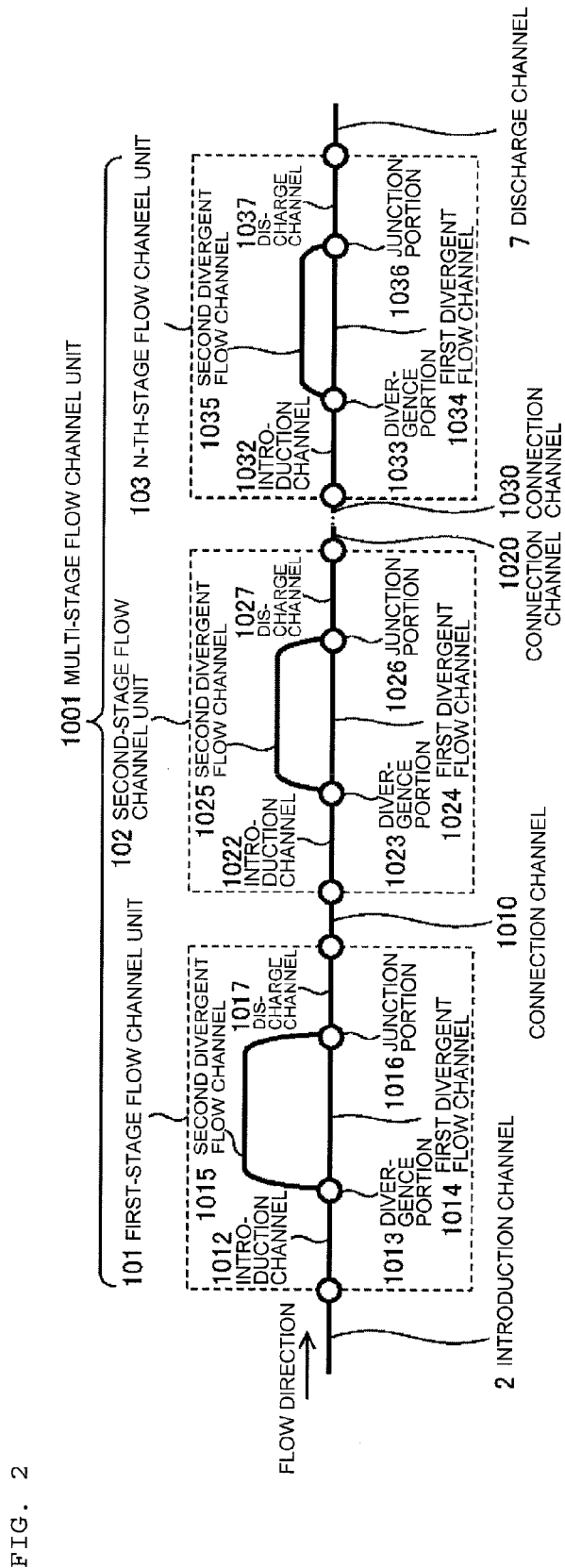
FIG. 2 is a configuration diagram illustrating a configuration of a flow channel in a mixer.

FIG. 2 is a configuration diagram illustrating a configuration of the flow channel in the mixer. FIG. 2 is a schematic diagram illustrating a multi-stage flow channel unit 1001 in which the multiple flow channel units 101, 102, and 103 are connected to each other with connection channels 1010, 1020 and 1030. One flow channel unit includes an introduction channel 2, a branch portion 3, a first branched flow channel 4, a second branched flow channel 5, a junction portion 6, and a discharge channel 7. The flow channel unit 103 indicates the n-th-stage flow channel unit, and the number of stages is arbitrarily determined.

In a case of the multi-stage flow channel unit, the discharge channel in the upper-stage flow channel unit and the introduction channel in the flow channel unit below the upper-stage flow channel unit are connected to each other with the connection channel. It is not necessarily required to prepare a special configuration as the connection channel and one flow channel may serve also as the discharge channel in the upper-stage flow channel unit, the introduction channel in the flow channel unit below the upper-stage flow channel unit and the connection channel. Furthermore, the mixer, which is generally known and realizes the mixing in the width direction with respect to the flow channel, may be connected between the flow channel units, in front of and behind the flow channel unit, when necessary. The multi-stage flow channel unit is formed by laminating the flow channel substrate in which one flow channel unit is formed with a structure having the flow channel equivalent to the connection channel when necessary being interposed. Otherwise, the multi-stage flow channel unit is realized also by forming the multiple flow channel units, each including the connection channel on one flow channel substrate.

FIGS. 3 to 9 illustrate an example of a shape of the flow channel substrate in which one flow channel unit is formed. Though not illustrated in the drawings, the inside of the flow channel in the flow channel unit may be filled with, for example, a porous material, or may be empty. The multiple flow channel substrates 14 having various shapes of groove, illustrated in FIGS. 3 to 9 are combined, in such a manner as to provide a necessary flow channel length as illustrated in FIG. 2, to configure the multi-stage flow channel unit.

Figure 3:
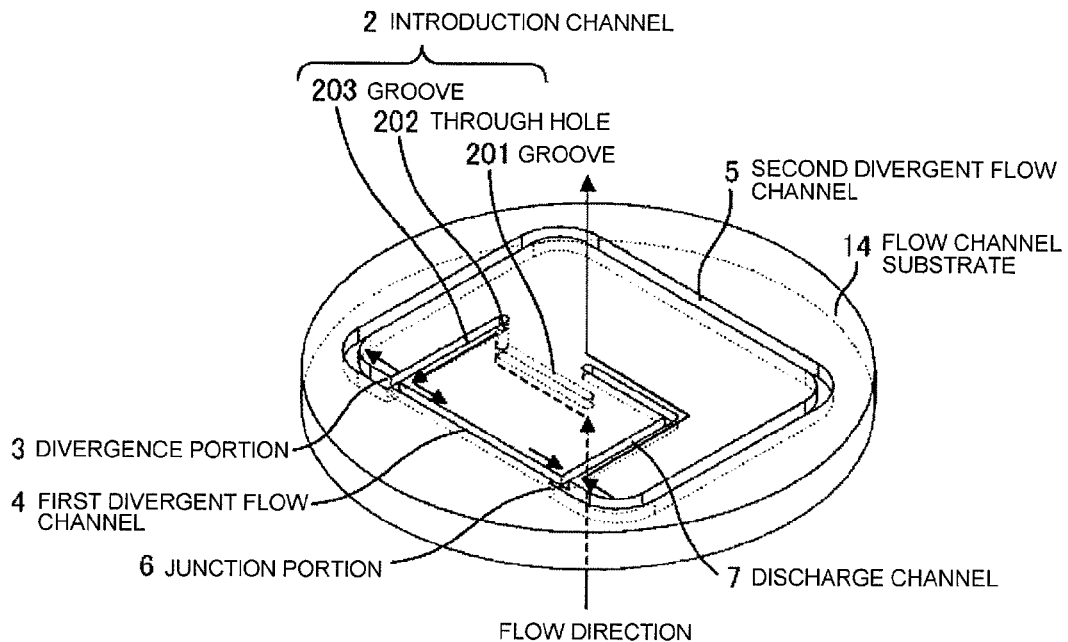
FIG. 3 is a perspective view illustrating a configuration of a flow channel substrate.

FIG. 3 is a perspective view illustrating a configuration of the flow channel substrate, and illustrates the flow channel unit in which the first branched flow channel 4 is linear and the second branched flow channel 5 is bent in three places. The introduction channel 2 includes a groove 201 formed in the lower surface of the flow channel substrate 14, a through hole 202 piercing through the lower surface and the upper surface of the flow channel substrate 14, and a groove 203 formed in a surface of the flow channel substrate 14. The first branched flow channel 4, the second branched flow channel 5, and the discharge channel 7 are formed as the grooves in the upper surface of the flow channel substrate 14. A liquid branches in the branch portion 3 after flowing through the introduction channel 2, joins in the junction portion 6 after flowing through the first branched flow channel 4 or the second branched flow channel 5 and is discharged from the flow channel unit after flowing through the discharge channel 7.

Figure 4:
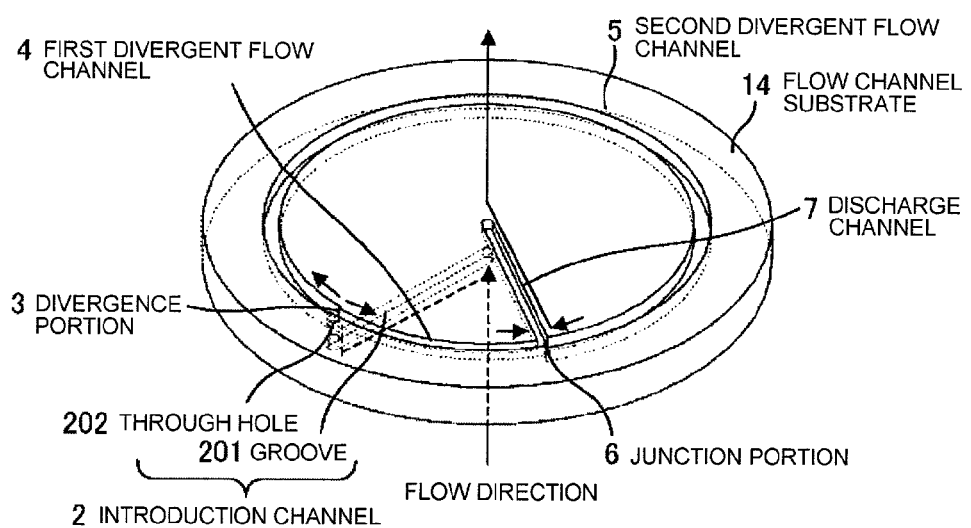
FIG. 4 is a perspective view illustrating the configuration of the flow channel substrate.

FIG. 4 is perspective view illustrating the configuration of the flow channel substrate, and is the flow channel unit in which the first branched flow channel 4 and the second branched flow channel 5 are in the shape of a circle. The introduction channel 2 includes the groove 201 formed in the lower surface of the flow channel substrate 14, and the through hole 202 piercing through the lower surface and the upper surface of the flow channel substrate 14. The first branched flow channel 4, the second branched flow channel 5, and the discharge channel 7 are formed as the grooves in the upper surface of the flow channel substrate 14. The liquid branches in the branch portion 3 after flowing through the introduction channel 2, joins in the junction portion 6 after flowing through the first branched flow channel 4 or through the second branched flow channel 5 and is discharged from the flow channel unit after flowing through the discharge channel 7.

Figure 5:
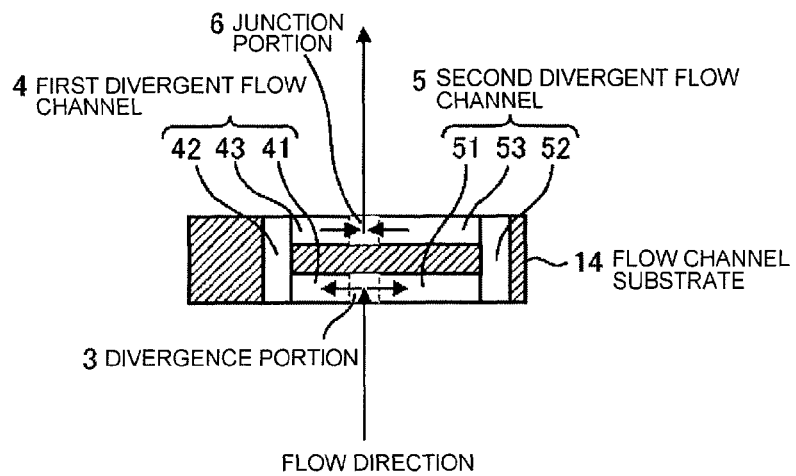
FIG. 5 is a cross-sectional view illustrating the configuration of the flow channel substrate.

FIG. 5 is a cross-sectional view illustrating the configuration of the flow channel substrate. The flow channel substrate 14 has the first branched flow channel 4 including a groove 41 in the lower surface of the flow channel substrate 14, a through hole 42 piercing through the lower surface and the upper surface, and a groove 43 in the upper surface, and the second branched flow channel 5 including a groove 51 in the lower surface of the flow channel substrate 14, a through hole 52 piercing through the lower surface and the upper surface, and a groove 53 in the upper surface.

Figure 6:
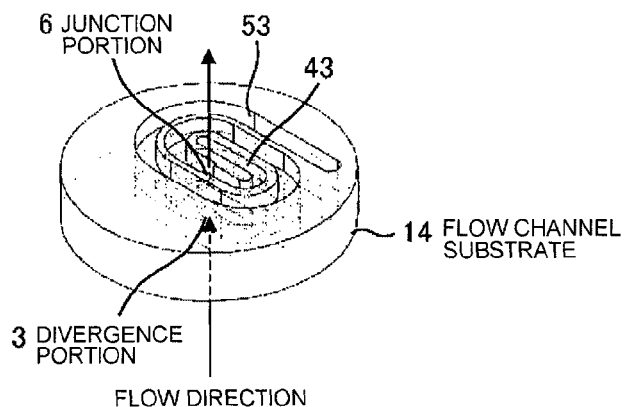
FIG. 6 is a perspective view illustrating the configuration of the flow channel substrate.

FIG. 6 is a perspective view illustrating the configuration of the flow channel substrate, and illustrating shapes of the groove 43 in the upper surface and the groove 53 in the upper surface that are illustrated in FIG. 5. The grooves in the upper surface are formed in the shape of a spiral. The lower surface is also formed in the same configuration.

Figure 7:
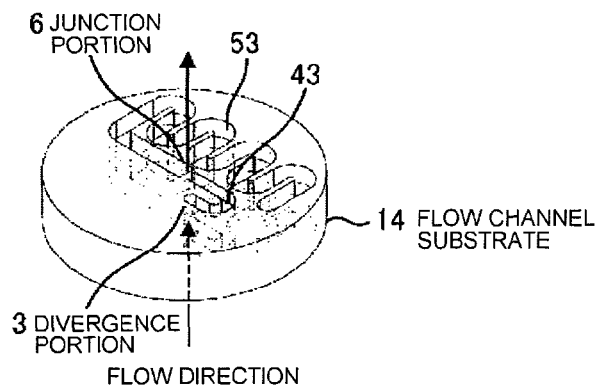
FIG. 7 is a perspective view illustrating the configuration of the flow channel substrate.

FIG. 7 is a perspective view illustrating the configuration of the flow channel substrate, and illustrating the shapes of the groove 43 in the upper surface and the groove 53 in the upper surface that are illustrated in FIG. 5. The grooves in the upper surface are formed in the shape of a wave line. The lower surface is also formed in the same configuration.

Figure 8:
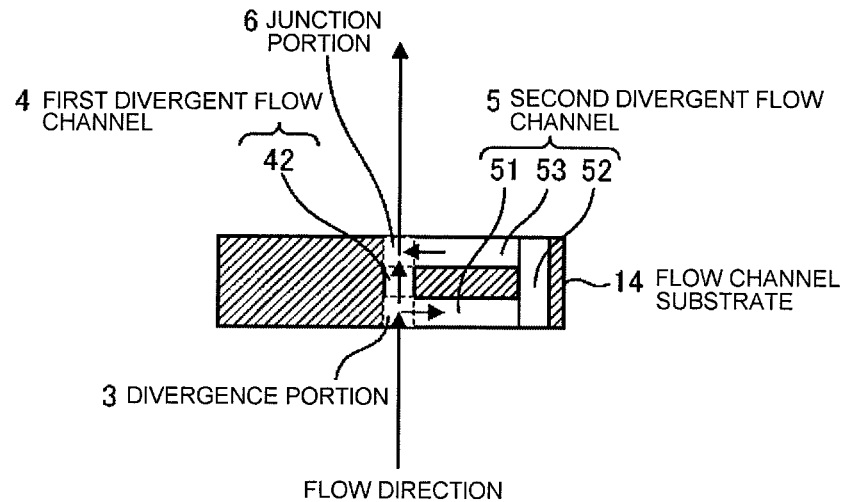
FIG. 8 is a cross-sectional view illustrating the configuration of the flow channel substrate.

FIG. 8 is a cross-sectional view illustrating the configuration of the flow channel substrate. The flow channel substrate 14 has the first branched flow channel 4 including the through hole 42 piercing through the lower surface and the upper surface of the flow channel substrate 14, and the second branched flow channel 5 including the groove 51 in the lower surface of the flow channel substrate 14, the through hole 52 piercing through the lower surface and the upper surface, and the groove 53 in the upper surface.

Figure 9:
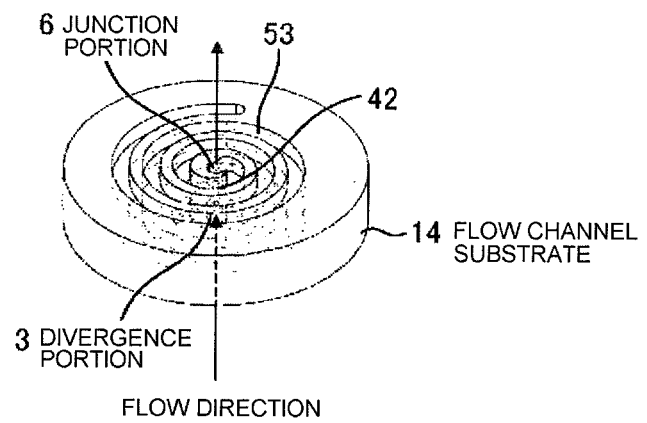
FIG. 9 is a perspective view illustrating the configuration of the flow channel substrate.

FIG. 9 is a perspective view illustrating the configuration of the flow channel substrate, and illustrating the shapes of the through hole 42 and the groove 53 in the upper surface that are illustrated in FIG. 8. The groove 53 in the upper surface is formed in the shape of a spiral. The lower surface is also formed in the same configuration.

Since in the configuration of the flow channel unit illustrated in FIGS. 5 to 9, the flow channel may be formed as both of the grooves in the lower surface and the upper surface of the flow channel substrate 14, and the through hole in the lower surface and the upper surface, in a case where a flow channel with the same volume is formed, the substrate area may be decreased, compared to a configuration in which the flow channel is formed, as the groove, only in either of the lower surface and the upper surface of the flow channel substrate as illustrated in FIGS. 3 and 4. At this time, as illustrated in FIG. 1, in a case where hydraulic pressure is sealed by pressing the flow channel substrate 14, with the housing lid 1201 and the housing bottom 1202, a higher hydraulic pressure may be sealed because the surface pressure added to the flow channel substrate 14 is increased. Furthermore, the external shapes of the housing lid 1201 and the housing bottom 1202 may be also decreased, and it is possible to decrease the external shape of the entire mixer and thus a degree of freedom in an arrangement of the components in the liquid chromatograph may be increased.

Figure 10:
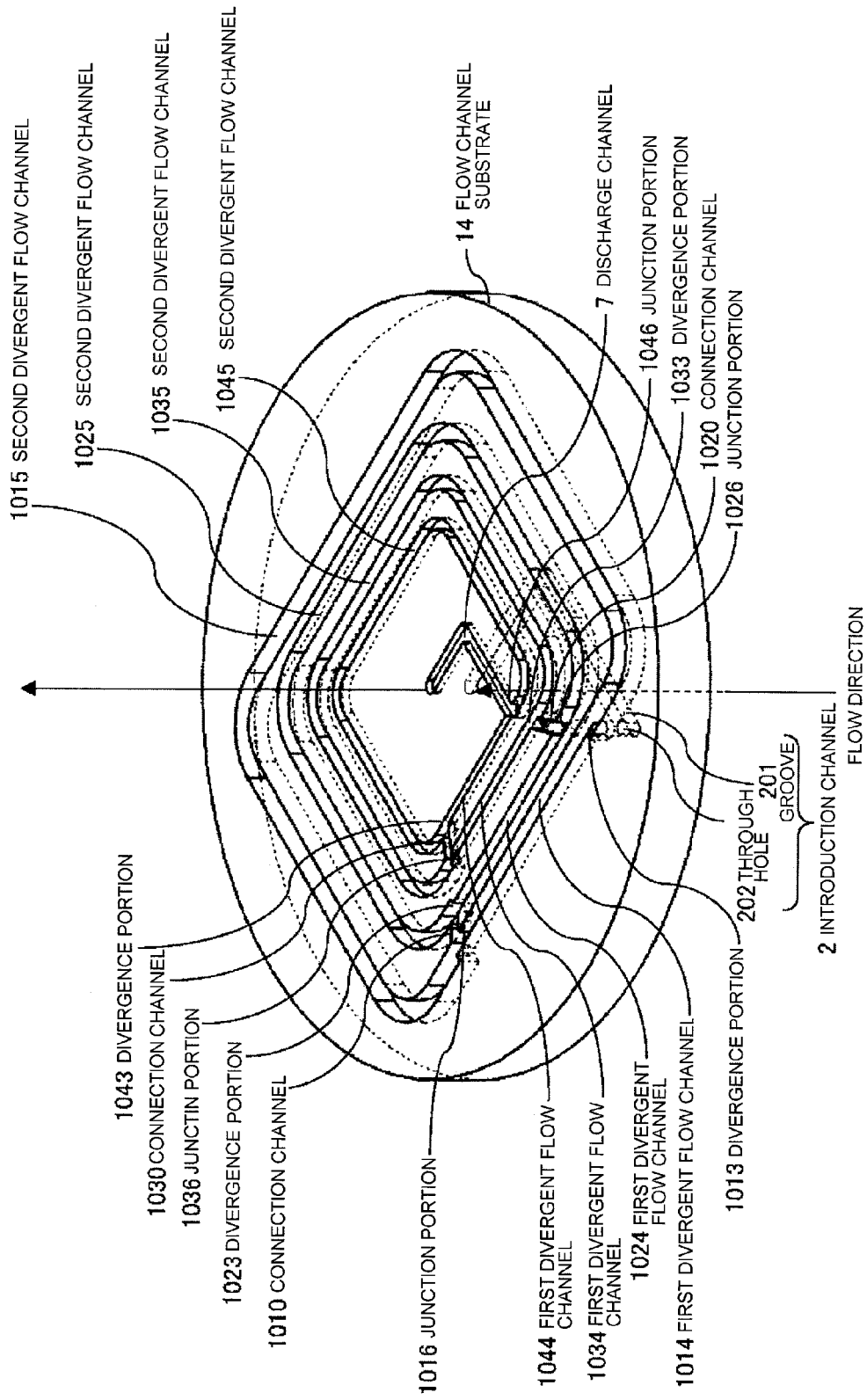
FIG. 10 is a perspective view illustrating the configuration of the flow channel substrate.
Figure 11:
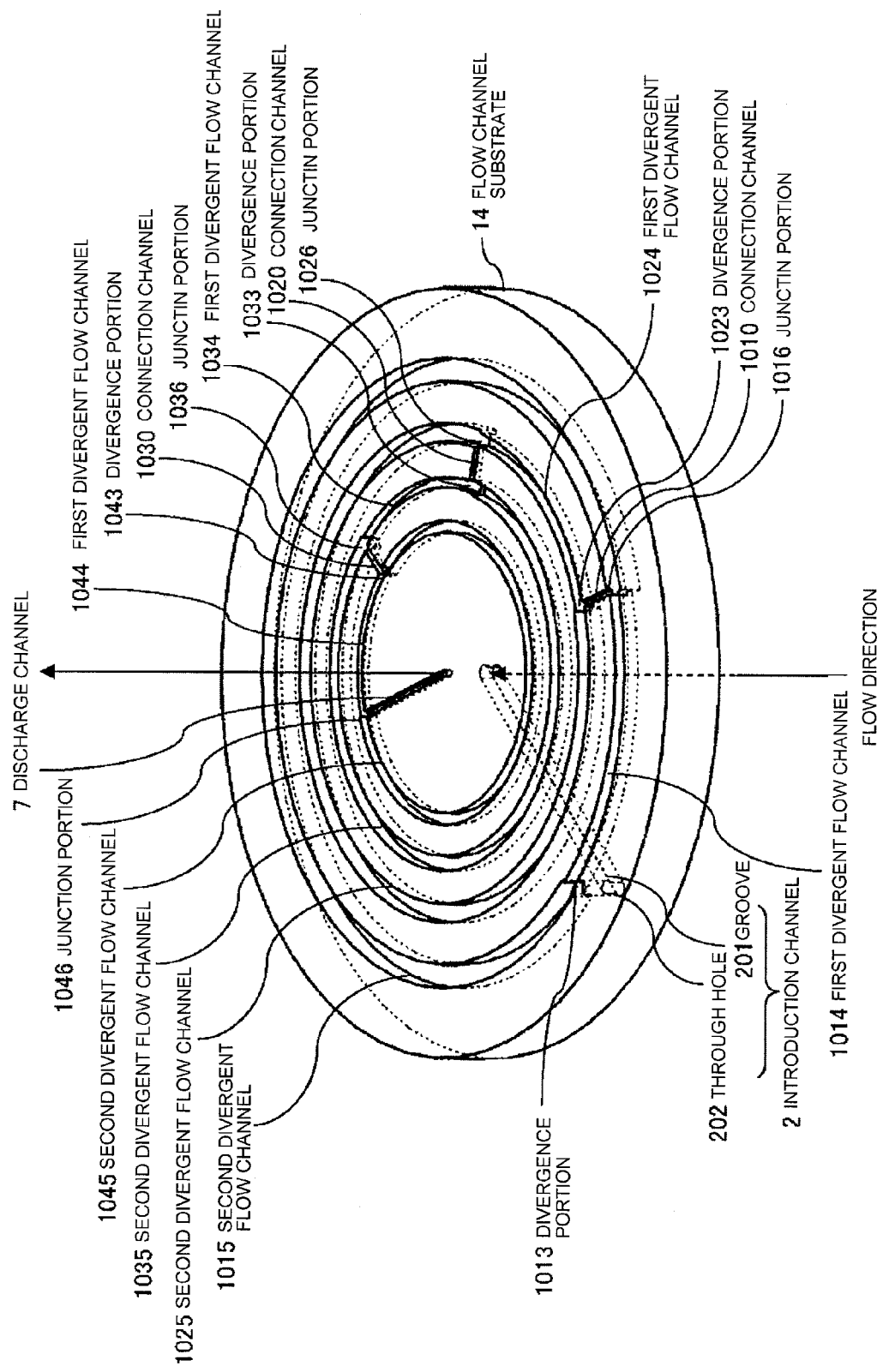
FIG. 11 is a perspective view illustrating the configuration of the flow channel substrate.

FIGS. 10 and 11 are perspective views illustrating the configurations of the flow channel substrates and examples of the shape of the flow channel substrate in which the multi-stage flow channel unit is formed. The multi-stage flow channel unit, formed as illustrated in FIG. 10, includes the introduction channel 2, a first-stage flow channel unit 101, a second-stage flow channel unit 102, a third-stage flow channel unit 103, a fourth-stage flow channel unit 104, the connection channels 1010, 1020, and 1030 that connect the flow channel units at each stage to one another, and the discharge channel 7. The introduction channel 2 includes the groove 201 formed in the lower surface of the flow channel substrate 14, and the through hole 202 piercing through the lower surface and the upper surface of the flow channel substrate 14. Each of the flow channel units 101, 102, 103, and 104 includes the branch portion, the first branched flow channel, the second branched flow channel, and the junction portion, which are formed, as the grooves, in the upper surface of the flow channel substrate 14. Each of the flow channel units 101, 102, 103, and 104 is a flow channel unit in which the first branched flow channel is linear and in which the second branched flow channel is bent at three places. The discharge channel 7 is formed, as the groove, in the upper surface of the flow channel substrate 14.

The liquid branches in a branch portion 1013 of the first-stage flow channel unit 101 after flowing through the introduction channel 2, joins in a junction portion 1016 after flowing through a first branched flow channel 1014 or through a second branched flow channel 1015, branches in the branch portion 1023 of the second-stage flow channel unit 102 after flowing through a connection channel 1010, joins in a junction portion 1026 after flowing through a first branched flow channel 1024 or a second branched flow channel 1025, branches in a branch portion 1033 of the third-stage flow channel unit 103 after flowing through a connection channel 1020, joins in a junction portion 1036 after flowing through a first branched flow channel 1034 or a second branched flow channel 1035, branches in a branch portion 1043 of a fourth-stage flow channel unit 104 after flowing through a connection channel 1030, joins in a junction portion 1046 after flowing through a first branched flow channel 1044 or through a second branched flow channel 1045, and is discharged from the flow channel unit after flowing through the discharge channel 7.

The multi-stage flow channel unit, formed as illustrated in FIG. 11, includes the introduction channel 2, the first-stage flow channel unit 101, the second-stage flow channel unit 102, the third-stage flow channel unit 103, the fourth-stage flow channel unit 104, the connection channels 1010, 1020, and 1030 that connect the flow channel units at each stage to one another, and the discharge channel 7. The introduction channel 2 includes the groove 201 formed in the lower surface of the flow channel substrate 14, and the through hole 202 piercing through the lower surface and the upper surface of the flow channel substrate 14. Each of the flow channel units 101, 102, 103, and 104 includes the branch portion, the first branched flow channel, the second branched flow channel, and the junction portion, each of which is formed as a groove, in the upper surface of the flow channel substrate 14. Each of the flow channel units 101, 102, 103, and 104, is a flow channel unit in which the first branched flow channel 4 and the second branched flow channel 5 are in the shape of a circle.

As described above, an example in which one flow channel unit is formed in one flow channel substrate is illustrated in FIGS. 5 to 9, and an example in which the multiple flow channel units are formed in one flow channel substrate is illustrated in FIGS. 10 and 11. In addition to what is described above, as the method of forming the flow channel unit in the flow channel substrate, for example, the flow channel may be formed as illustrated in FIGS. 5 to 11 by configuring one flow channel unit with the multiple flow channel substrates, or by configuring one flow channel unit with a spacer arranged between the multiple flow channel substrates.

Figure 12:
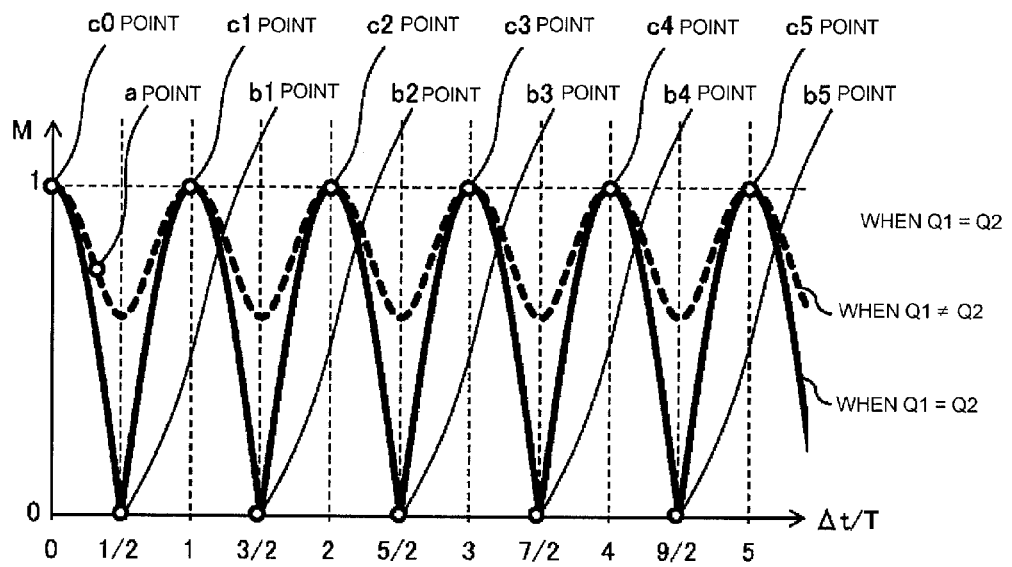
FIG. 12 is a graph showing the performance of decreasing a concentration non-uniformity in the flow direction.

FIG. 12 is a graph showing the performance of decreasing a concentration non-uniformity in the flow direction. T is the period of the concentration non-uniformity, Δt is the difference between the time t1 for the liquid to pass through the first branched flow channel and the time t2 for the liquid to pass through the second branched flow channel, and M is the performance of decreasing the concentration non-uniformity in the flow direction, expressed in Equation 13 described below.

Based on the embodiment of the present invention, principle is described that the concentration non-uniformity in the flow direction is decreased using the mixer. First, the principle is described that the concentration non-uniformity in the flow direction is decreased using one flow channel unit in a case where a flow velocity inside the flow channel is constant.

For example, the time t1 for the liquid to pass through the first branched flow channel 4 in the flow channel unit illustrated in FIG. 4, and the time t2 for the liquid to pass through the second branched flow channel 5 are expressed as the following equations, using flow rate Q1 and Q2 and volumes V1 and V2, respectively.

$$t1 = V1/Q1 \quad \text{(Equation 1)}$$

$$t2 = V2/Q2 \quad \text{(Equation 2)}$$

At this time, in a case where the concentration Cin of the branch portion is changed over time in a sine waveform where the concentration of the center portion is C0, the amplitude of the concentration is Ca, and the period of the concentration is T, the concentration Cin of the branch portion is expressed, with time being set to t, as the following equation.

$$Cin = C0 + Ca \cdot \sin(2\pi t/T) \quad \text{(Equation 3)}$$

The concentration C1out in an outlet of the first branched flow channel and the concentration C2out in an outlet of the second branched flow channel are expressed as the following equations, respectively.

$$C1out = C0 + Ca \cdot \sin(2\pi(t-t1)/T) \quad \text{(Equation 4)}$$

$$C2out = C0 + Ca \cdot \sin(2\pi(t-t2)/T) \quad \text{(Equation 5)}$$

At this point, when the amount of substance which flows through a certain cross-section of the flow channel per unit time is called flux, flux J1 of the outlet of the first branched flow channel and flux J2 of the outlet of the second branched flow channel are expressed as the following equations.

$$\begin{aligned} J1 &= C1out \cdot Q1 \\ &= C0 \cdot Q1 + Ca \cdot Q1 \cdot \sin(2\pi(t-t1)/T) \end{aligned} \quad \text{(Equation 6)}$$

$$\begin{aligned} J2 &= C2out \cdot Q2 \\ &= C0 \cdot Q2 + Ca \cdot Q2 \cdot \sin(2\pi(t-t2)/T) \end{aligned} \quad \text{(Equation 7)}$$

Therefore, the concentration Cout of the junction portion is obtained using the following equation.

$$\begin{aligned} Cout &= (J1 + J2)/(Q1 + Q2) \\ &= C0 + (Ca/(Q1+Q2)) \cdot \\ & \quad (A \cdot \sin(2\pi t/T) - B \cdot \sin(2\pi t/T)) \end{aligned} \quad \text{(Equation 8)}$$

At this point, it is determined that tan α=B/A.

$$A = Q1 \cdot \cos(2\pi t1/T) + Q2 \cdot \cos(2\pi t2/T) \quad \text{(Equation 9)}$$

$$B = Q1 \cdot \sin(2\pi t1/T) + Q2 \cdot \sin(2\pi t2/T) \quad \text{(Equation 10)}$$

$$\begin{aligned} Cout &= C0 + (Ca/(Q1+Q2)) \cdot \left(\sqrt{(A^2+B^2)}\sin(2\pi t/T - \alpha)\right) \\ &= C0 + (Ca/(Q1+Q2)) \cdot \\ & \quad \sqrt{(Q1^2 + Q2^2 + 2Q1 \cdot Q2(\cos(2\pi t1/T - 2\pi t2/T)))} \cdot \\ & \quad \sin(2\pi t/T - \alpha) \end{aligned} \quad \text{(Equation 11)}$$

At this point, it is determined that αt=t2−t1.

$$Cout = C0 + (Ca/(Q1+Q2)) \cdot \sqrt{(Q1^2+Q2^2+2Q1 \cdot Q2 \cdot \cos(2\pi \Delta t/T))} \cdot \sin(2\pi t/T - \alpha) \quad \text{(Equation 12)}$$

At this point, the amplitude of the change over time in the concentration in the junction portion, that is, the size of the concentration non-uniformity is determined as follows.

$$Cb = (Ca/(Q1+Q2)) \cdot \sqrt{(Q1^2+Q2^2+2Q1 \cdot Q2 \cdot \cos(2\pi \Delta t/T))}.$$

$$Cout = C0 + Cb \cdot \sin(2\pi t/T - \alpha) \quad \text{(Equation 13)}$$

The performance of decreasing the concentration non-uniformity in the flow direction in the flow channel unit is defined as the ratio M of the amplitude Cb of the concentration in the junction portion to the amplitude Ca of the concentration in the branch portion, and is expressed as the following equation.

$$M=Cb/Ca=(1/(Q1+Q2))\cdot\sqrt{(Q1^2+Q2^2+2Q1\cdot Q2\cdot\cos(2\pi\Delta t/T))} \quad \text{(Equation 14)}$$

For example, when the performance M of decreasing the concentration non-uniformity in the flow direction is 1, this means that the concentration non-uniformity in the flow direction is not decreased. Furthermore, when M is 0, this means that the concentration non-uniformity in the flow direction is completely decreased and the concentration non-uniformity is not present in the junction portion.

When the ratio $\Delta t/T$ of the difference $\Delta t$ between the time t1 for the liquid to pass through the first branched flow channel and the time t2 for the liquid to pass through the second branched flow channel to the concentration non-uniformity period T is not an integer (0, 1, 2, and so forth), M<1 and the concentration non-uniformity in the flow direction due to the flow channel unit is decreased. For example, at the point a in FIG. 12, the ratio $\Delta t/T$ of the difference $\Delta t$ between the time t1 for the liquid to pass through the first branched flow channel and the time t2 for the liquid to pass through the second branched flow channel to the concentration non-uniformity period T is a value between 0 and ½ (0<($\Delta t/T$)<½) and furthermore, the amount Q1 of the liquid flowing through the first branched flow channel and the amount Q2 of the liquid flowing through the second branched flow channel are different from each other (Q1≠Q2).

Specifically, when the ratio $\Delta t/T$ of the difference $\Delta t$ between the time t1 for the liquid to pass through the first branched flow channel and the time t2 for the liquid to pass through the second branched flow channel to the concentration non-uniformity period T is the sum of an integer and ½ (½, ³⁄₂, ⁵⁄₂, and so forth), and furthermore, the amount Q1 of the liquid flowing through the first branched flow channel and the amount Q2 of the liquid flowing through the second branched flow channel are equal to each other (Q1=Q2), M=0, and the concentration non-uniformity in the flow direction is completely decreased and the concentration non-uniformity in the flow direction is not present in the junction portion. For example, at the point b1, the point b2, the point b3, the point b4, and the point b5 in FIG. 2, the ratios $\Delta t/T$ of the difference $\Delta t$ between the time t1 for the liquid to pass through the first branched flow channel and the time t2 for the liquid to pass through the second branched flow channel to the concentration non-uniformity period T are ½, ³⁄₂, ⁵⁄₂, ⁷⁄₂, ⁹⁄₂, respectively, and furthermore, the amount Q1 of the liquid flowing through the first branched flow channel and the amount Q2 of the liquid flowing through the second branched flow channel are equal to each other (Q1=Q2).

When the ratio $\Delta t/T$ of the difference $\Delta t$ between the time t1 for the liquid to pass through the first branched flow channel and the time t2 for the liquid to pass through the second branched flow channel to the concentration non-uniformity period T is an integer (0, 1, 2, and so forth), M=1, and the concentration non-uniformity in the flow direction due to the flow channel unit is not decreased. For example, at the point c0, the point c1, the point c2, the point c3, the point c4, and the point c5 in FIG. 2, the ratios $\Delta t/T$ of the difference $\Delta t$ between the time t1 for the liquid to pass through the first branched flow channel and the time t2 for the liquid to pass through the second branched flow channel to the concentration non-uniformity period T are 0, 1, 2, 3, 4, and 5, respectively.

Next, the condition is described for the flow channel structure to differentiate between the time t1 for the liquid to pass through the first branched flow channel and the time t2 for the liquid to pass through the second. In (Equation 1) and (Equation 2) that are described above, the following equation is produced from t1≠t2.

$$V1/Q1 \neq V2/Q2 \quad \text{(Equation 15)}$$

Therefore, the ratio for the amount of the flowing liquid is expressed as the following equation.

$$Q1/Q2 \neq V1/V2 \quad \text{(Equation 16)}$$

When the pressure loss of the flow channel is defined as $\Delta P$ and the amount of the flowing liquid as Q, the fluid resistance R of the flow channel is expressed as the following equation.

$$R=\Delta P/Q \quad \text{(Equation 17)}$$

Therefore, when the fluid resistance in the first branched flow channel is defined as R1 and the fluid resistance in the second branched flow channel as R2, a combined fluid resistance R in the first branched flow channel and the second branched flow channel is expressed as the following equation.

$$R=R1\cdot R2/(R1+R2) \quad \text{(Equation 18)}$$

Furthermore, the amount Q1 of the liquid flowing through the first branched flow channel and the amount Q2 of the liquid flowing through the second branched flow channel are expressed as the following equations.

$$Q1=(R2/R)\cdot(Q1+Q2) \quad \text{(Equation 19)}$$

$$Q2=(R1/R)\cdot(Q1+Q2) \quad \text{(Equation 20)}$$

Therefore, the ratio for the amount of the flowing liquid is expressed as the following equation.

$$Q1/Q2=R2/R1 \quad \text{(Equation 21)}$$

At this point, when the cross-sectional area of the first branched flow channel is defined as A1, the length as L1, the fluid resistance per unit cross-sectional area unit length as $\rho 1$, the cross-sectional area of the second branched flow channel as A2, length as L2, fluid resistance per unit cross-sectional area unit length as $\rho 2$, the fluid resistances R1 and R2 of the first and second branched flow channels are expressed as the following equations, respectively.

$$R1=\rho 1\cdot L1/A1 \quad \text{(Equation 22)}$$

$$R2=\rho 2\cdot L2/A2 \quad \text{(Equation 23)}$$

Therefore, the ratio for the amount of the flowing liquid is expressed as the following equation.

$$Q1/Q2=\rho 2\cdot L2\cdot A1/(\rho 1\cdot L1\cdot A2) \quad \text{(Equation 24)}$$

Next, when the porosity of the first branched flow channel is defined as $\phi 1$ and the porosity of the second branched flow channel as $\phi 2$, volumes V1 and V2 of the first and second branched flow channels are expressed as the following equations, respectively.

$$V1=\phi 1\cdot A1\cdot L1 \quad \text{(Equation 25)}$$

$$V2=\phi 2\cdot A2\cdot L2 \quad \text{(Equation 26)}$$

When Equation 16 is rewritten using Equation 24, Equation 25 and Equation 26, this is expressed as the following equation.

$$\rho 2\cdot L2\cdot A1/(\rho 1\cdot L1\cdot A2) \neq \phi 1\cdot A1\cdot L1/(\phi 2\cdot A2\cdot L2) \quad \text{(Equation 27)}$$

When the rewriting is done in such a manner as to correspond to each of the branched flow channels, this is expressed as the following equation.

$$\rho 1/(\phi 1\cdot L1^2) \neq \rho 2/(\phi 2\cdot L2^2) \quad \text{(Equation 28)}$$

According to Equation 28, when the branched flow channels are different from each other in terms of a value $\rho/(\phi L^2)$ that is determined by the fluid resistance $\rho$ the porosity $\phi$, and the length L per unit cross-sectional area unit length, the time t1 for the liquid to pass through the first branched flow channel and the time t2 for the liquid to pass through the second branched flow channel are different from each other. Especially, when the first branched flow channel and the second branched flow channel are the same in terms of fluid resistance and porosity ($\rho1=\rho2$, and $\phi1=\phi2$) such as when each inside of the flow channels is filled with the same porous material, the time t1 for the liquid to pass through the first branched flow channel and the time t2 for the liquid to pass through the second branched flow channel are different from each other in a case where the first branched flow channel and the second branched flow channel are different in length (L1≠L2).

Next, the principle is described that the concentration non-uniformity in the flow direction is decreased in a case where the flow velocity inside the flow channel is constant and in a case where the flow channel units are connected to each other in multiple stages. With this configuration, the concentration non-uniformity decreased by the upper-state flow channel unit is further decreased by the lower-stage flow channel unit. Therefore, the performance of decreasing the concentration non-uniformity in the flow direction may be improved compared to the single-stage flow channel unit.

In a case where the n flow channel units making up the multi-stage flow channel unit 1001, that is, the flow channel units 101, 201 and 301, in FIG. 2, are in the same shape, the performances M of decreasing the concentration non-uniformity in the flow direction are all equal. At this time, the performance Mt of decreasing the concentration non-uniformity in the flow direction in the multi-stage flow channel unit 1001 is expressed as the following equation.

$$Mt=M^n \quad \text{(Equation 29)}$$

Therefore, the performance Mt of decreasing the concentration non-uniformity in the flow direction is improved by increasing the number n of stages of the flow channel unit. However, when the ratio $\Delta t/T$ of the difference $\Delta t$ between the time t1 for the liquid to pass through the first branched flow channel and the time t2 for the liquid to pass through the second branched flow channel to the concentration non-uniformity period T is an integer (0, 1, 2, and so forth) (the point c0, the point c1, the point c2, the point c3, the point c4 and the point c5 in FIG. 12 correspond to this case), Mt=1 without depending on the number of stages of the flow channel unit and the concentration non-uniformity in the flow direction is not decreased.

The case is considered where the n flow channel units making up the multi-stage flow channel unit 1001, that is, the flow channel units 101, 201, and 301 in FIG. 2 are different from each other in terms of the difference $\Delta t$ between the time t1 for the liquid to pass through the first branched flow channel and the time t2 for the liquid to pass through the second branched flow channel. When the performances of decreasing the concentration non-uniformity in the flow direction in the flow channel units 101, 201, and 301 are defined as M1, M2, and Mn, respectively, the performance Mt of decreasing the concentration non-uniformity in the flow direction in the multi-stage flow channel unit 1001 is expressed as the following equation.

$$Mt=M1 \cdot M2 \text{ and so forth up to } Mn \quad \text{(Equation 30)}$$

The differences $\Delta t$ between the time for the liquid to pass through one flow channel unit and the time for the liquid to pass through another are different in the multi-stage flow channel unit and the concentration non-uniformity period, in which the concentration non-uniformity in the flow direction is not decreased, and which corresponds to the point c1, the point c2, the point c3, the point c4, or the point c5 in FIG. 12, varies at the flow channel unit at each stage. Therefore, over the entire concentration non-uniformity period T, Mt<1 and the concentration non-uniformity Mt in the flow direction may be decreased.

In the multi-stage flow channel unit 1001, in the n flow channel units, all of which are connected to one another, the case is considered where the amount Q1 of the liquid flowing through the first branched flow channel and the amount Q2 of the liquid flowing through the second branched flow channel are equal to each other (Q1=Q2), and the difference $\Delta t(k)$ between the time t1 for the liquid to pass through the first branched flow channel and the time t2 for the liquid to pass through the second branched flow channel in the k-th-stage flow channel unit is half the difference $\Delta t(k-1)$ between the time t1 for the liquid to pass through the first branched flow channel and the time t2 for the liquid to pass through the second branched flow channel in the flow channel unit that is positioned one stage above the k-th-stage flow channel unit. The condition at this time is expressed as the following equation.

$$\Delta t(R-1)/2 = \Delta t(R) \quad \text{(Equation 31)}$$

In this case, in the condition that $0<\Delta t(1)/T<2^{n-1}$ in the period T of the concentration non-uniformity where the performance M of decreasing the concentration non-uniformity in the flow direction in the upper-stage flow channel unit is 1, the performance M of decreasing the concentration non-uniformity in the flow direction in the flow channel unit that is positioned below the upper-stage flow channel unit is 0. At this time, when the period T of the concentration non-uniformity is in the range that meets the condition that $0<1/T<2^{n-1}/\Delta t(1)$, Mt<1, and the concentration non-uniformity in the flow direction may be decreased. Especially, when the ratio $\Delta t(1)/T$ of the difference $\Delta t(1)$ between the time t1 for the liquid to pass through the first branched flow channel and the time t2 for the liquid to pass through the second branched flow channel in the first stage is a product (½, 1, 3/2, 2, 5/2, and so forth) of an integer and ½, Mt=0, the concentration non-uniformity in the flow direction is completely decreased and the concentration non-uniformity in the flow direction in the junction portion in the lowest-stage flow channel unit may be removed.

Next, the case is described where the flow velocity inside the flow channel of the mixer is nonconstant. In an actual flow channel, the flow velocity inside the flow channel is not completely constant due to the secondary flow or the flow separation that results from the friction of the inside wall of the flow channel, the curve of the flow channel, the branch, the junction, and more. Furthermore, in a case where there is no uniform structure such as a porous material, inside the flow channel, the flow velocity distribution is such that the flow velocity is at the maximum near the center of the flow channel, and at the minimum in the vicinity of the inside wall of the flow channel, because of the viscosity of the liquid. For this reason, the case where the nonconstant flow velocity distribution occurs and the case where the constant flow velocity distribution occurs are different in terms of the performance of the decrease in the flow direction.

Figure 13:
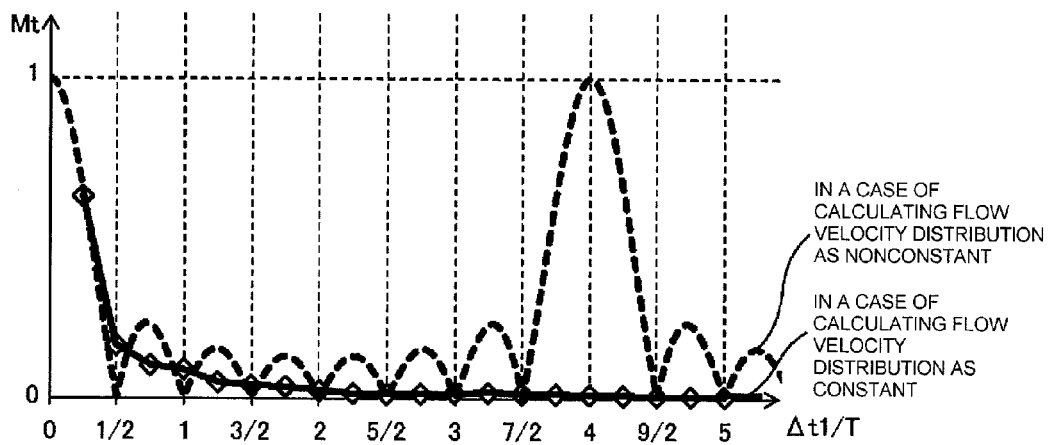
FIG. 13 is a graph showing the performance of decreasing the concentration non-uniformity in the flow direction.

FIG. 13 is a graph showing the performance of decreasing the concentration non-uniformity in the flow direction, and showing the result of calculating the decrease in the concentration non-uniformity in the flow direction when the flow velocity distribution is constant inside the flow channel and when the flow velocity distribution is nonconstant inside the flow channel, in a case where the flow channel unit has three stages, in all of the three flow channel units, connected to each other in the three stages, the amount Q1 of the liquid flowing through the first branched flow channel and the amount Q2 of the liquid flowing through the second branched flow channel are equal to each other (Q1=Q2), and the difference Δt (k) between the time t1 for the liquid to pass through the first branched flow channel and the time t2 for the liquid to pass through the second branched flow channel in the k-th-stage flow channel unit is half the difference Δt (k−1) between the time t1 for the liquid to pass through the first branched flow channel and the time t2 for the liquid to pass through the second branched flow channel in the flow channel unit that is positioned one stage above the k-th-stage flow channel unit.

In FIG. 13, a dotted line indicates the result of performing a simulation, with the flow velocity distribution being constant, and a solid line indicates the result of performing a simulation, with the flow velocity distribution being nonconstant. It is apparent that even though the flow-velocity distribution is nonconstant inside the flow channel, the concentration non-uniformity in the flow direction is Mt<1 and the concentration non-uniformity may be decreased.

The principle is described above that the concentration non-uniformity in the flow direction is decreased in a case of the flow channel unit with two branched flow channels in the flow channel unit, but this principle holds true for three or more branched flow channels, and when the times for the liquid to pass through the branched flow channels are different from each other, the same effect as in the case of the two branched flow channels may be obtained.

In the liquid chromatograph illustrated in FIG. 1, the effect described below may be obtained by properly selecting the characteristic of the performance Mt of decreasing the concentration non-uniformity in the flow direction with respect to the period T of the concentration non-uniformity in the flow direction in the multi-stage flow channel unit 1001 according to the behavior of the concentration non-uniformity in the flow direction due to the liquid sending pumps 2201 and 2202.

For example, in a case where the liquid sending pumps 2201 and 2202 are the same in specification, and send the liquid with a constant period, the decrease in the concentration non-uniformity in the flow direction may be realized by preparing the mixer that is made up of one flow channel unit.

Furthermore, for example, in a case where the liquid sending pumps 2201 and 2202 send the liquid with constant periods different from each other, the concentration non-uniformity in the flow direction is a result of an overlap of the two periods. With respect to each of the concentration non-uniformity changes of the two periods, the concentration non-uniformity in the flow direction may be decreased by preparing the mixer provided with the multi-stage flow channel unit including the flow channel unit that may decrease that period.

Furthermore, for example, in a case where the liquid sending pumps 2201 and 2202 send the liquid with the periods that change due to, for example, the amounts of the sent liquid, the concentration non-uniformity in the flow direction may be decreased by preparing the mixer provided with the multi-stage flow channel unit that is a result of combining the multiple flow channel units in such a manner that all of the concentration non-uniformity periods may be decreased.

Furthermore, for example, in a case where the change in the concentration non-uniformity in the flow direction due to the liquid sending pumps 2201 and 2202 is a result of the overlap of the multiple periods, the mixer is prepared that is provided with the multi-stage flow channel unit, produced by combining the flow channel units in such a manner as to decrease the concentration non-uniformity of each period, and thereby the concentration irregularities in the flow direction of all the periods, included by this configuration, may be decreased.

With the configuration and the operation of the mixer as described above, the concentration non-uniformity in the flow direction of the mobile phase may be decreased. As a result, in the liquid chromatograph using a light absorbance measuring instrument as a detector, there is an effect that a change in the detected light absorbance is small. Furthermore, in the liquid chromatograph using a fluorescent detector as the detector, there is an effect that a change in the detected fluorescence is small. Furthermore, in the liquid chromatograph using a differential refraction detector as the detector, there is an effect that a change in the detected refractive index is small. Due to the effects described above, a smaller amount of a sample may be detected and the sensitivity of the liquid chromatograph may be improved. Furthermore, because the area of a sample peak may be measured more accurately, there is an effect that the accuracy of the quantitative measurement is improved.

Furthermore, according to this example, the flow channel volume of the mixer may be decreased. For this reason, the period of time from when the mobile phase is introduced into the mixer to when the mobile phase is discharged is shortened, and the time necessary to perform a one-time analysis is shortened. Furthermore, in a case of the analysis using a gradient elution method, an effect is brought about that the concentration change of the mobile phase, closer to an ideal, may be generated.

According to this example, the mixer has a period in which the performance of decreasing the concentration non-uniformity in the flow direction of the mobile phase is at the maximum. Since the shorter the period is, the smaller the volume of the flow channel may be, the effect resulting from the decrease in the flow channel volume may be accomplished at the maximum by a system of the liquid chromatograph that drives the liquid sending pump in such a manner as to minimize the period of the concentration non-uniformity.

Example 2

Figure 14:
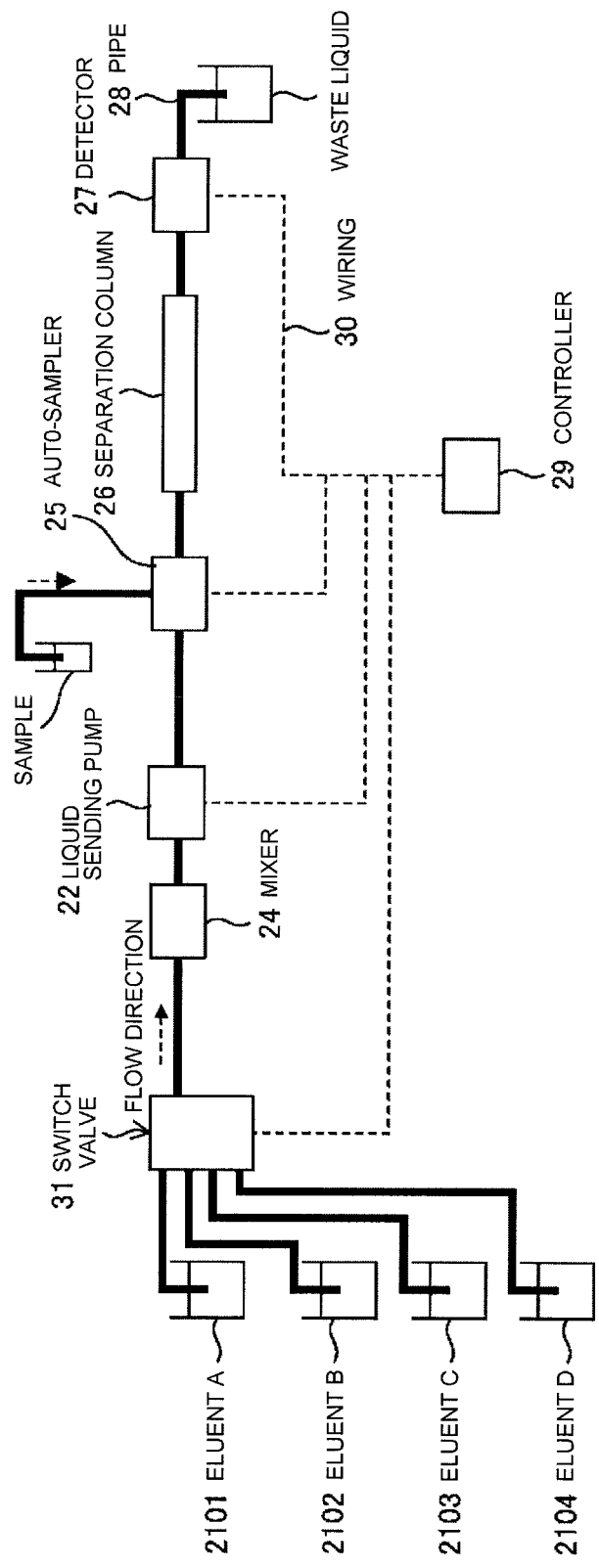
FIG. 14 is a configuration diagram illustrating the main configuration of the liquid chromatograph for a low pressure gradient elution method.

FIG. 14 is a configuration diagram illustrating a main configuration of a liquid chromatograph for a low pressure gradient elution method. The liquid chromatograph includes multiple eluents, for example, four kinds of eluents, that is, eluents A2101, B2102, C2103, and D2104, a switch valve 31, a mixer 24, a liquid sending pump 22, an auto-sampler 25, a separation column 26, a detector 27, a pipe 28 that connects components to one another in a manner that enables the liquid to flow, a controller 29 that controls each component, and wiring 30 that electrically connects components to one another. The four kinds of eluents are mixed in such a manner that the concentration non-uniformity is decreased by the mixer 24.

Figure 15:
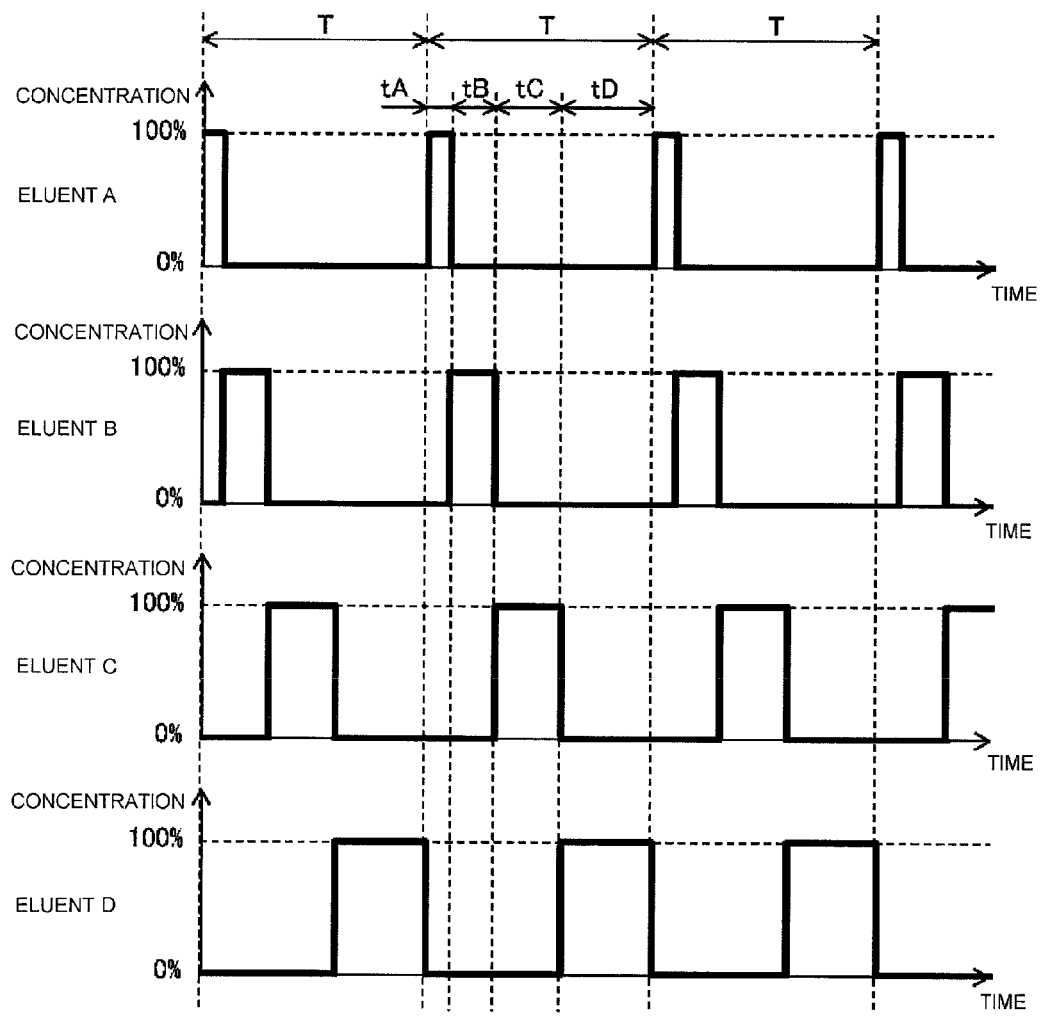
FIG. 15 is a graph showing concentration changes of eluents in the low pressure gradient elution method.

FIG. 15 is a graph showing concentration changes of the eluents in the low pressure gradient elution method. The low pressure gradient elution method changes the eluent sent from the liquid sending pump 22 using the switch valve 31. For this reason, for example, the change overtime of the concentration of the mobile phase in the inlet of mixer 24 is illustrated in FIG. 15. At this time, it is assumed that the eluent A, the eluent B, the eluent C, and the eluent D are sent in this order and the sending period is defined as T. In one period, the concentrations of the eluent A, the eluent B, the eluent C, and the eluent D in the mobile phase are adjusted by the times tA, tB, tC, and tD when the eluent A, the eluent B, the eluent C, and the eluent D are sent, respectively. At this time, inside the pipe that is positioned further downstream than the switch valve 31, the concentration non-uniformity of each of the eluents is generated in the concentration non-uniformity period T in the flow direction. For example, the concentration change of the eluent A is expressed as a square wave as illustrated in FIG. 15. The square wave of the period T may be expressed as an overlap of a sinusoidal wave of the period T, and a sinusoidal wave of a higher harmonic cycle (periods T/2, T/3, T/4, and so forth). When C1, C2, C3, and so forth, are defined as the amplitudes of the components of the periods T, T/2, T/3, and so forth, respectively, the concentration change C(A) of the eluent A is expressed as the following equation.

$$C \cdot (A) = C1 \cdot \sin(2\pi t/T) + C2 \cdot \sin(2\pi t/(T/2)) + C3 \cdot \sin(2\pi t/(T/3))$$ (Equation 32)

Therefore, the concentration non-uniformity of the eluent A may be decreased by the mixer that uses the multi-stage flow channel unit 1001 illustrated in FIG. 2. Similarly, the concentration irregularities of the eluent A, the eluent B, the eluent C, and the eluent D may be also decreased by the mixer that uses the multi-stage flow channel unit 1001 illustrated in FIG. 2.

With the configuration and the operation of the mixer as described above, the concentration non-uniformity in the flow direction of the mobile phase may be decreased. As a result, in the liquid chromatograph using a light absorbance measuring instrument as a detector, there is an effect that a change in the detected light absorbance is small. Furthermore, in the liquid chromatograph using a fluorescent detector as the detector, there is an effect that a change in the detected fluorescence is small. Furthermore, in the liquid chromatograph using a differential refraction detector as the detector, there is an effect that a change in the detected refractive index is small. Due to the effects described above, a smaller amount of a sample may be detected and the sensitivity of the liquid chromatograph may be improved. Furthermore, because the area of a sample peak may be measured more accurately, there is an effect that the accuracy of the quantitative measurement is improved.

Furthermore, according to this example, the flow channel area of the mixer may be decreased. For this reason, the period of time from when the mobile phase is introduced into the mixer to when the mobile phase is discharge is shortened, and the time necessary to perform a one-time analysis is shortened. Furthermore, in a case of the analysis using the gradient elution method, an effect is brought about that the concentration change of the mobile phase, closer to an ideal, may be generated.

According to this example, the mixer has a period in which the performance of decreasing the concentration non-uniformity in the flow direction of the mobile phase is at the maximum. Since the shorter the period is, the smaller the volume of the flow channel may be, the effect resulting from the decrease in the flow channel volume may be accomplished at the maximum by determining the period of the switch valve in such a manner as to minimize the period of the concentration non-uniformity.

As described above, according to the embodiment of the present invention, a liquid mixing device that decreases the concentration non-uniformity in the flow direction of the mobile phase and a liquid chromatograph using the liquid mixing device may be provided.

As a result, in the liquid chromatograph using a light absorbance measuring instrument as a detector, a change in the detected light absorbance is small. Furthermore, in the liquid chromatograph using a fluorescent detector as the detector, a change in the detected fluorescence is small. Furthermore, in the liquid chromatograph using a differential refraction detector as the detector, a change in the detected refractive index is small. Due to the effects described above, a smaller amount of a sample may be detected and the sensitivity of the liquid chromatograph is improved. Furthermore, because the area of a sample peak may be measured more accurately, the accuracy of the quantitative measurement is improved.

Furthermore, the mixer disclosed according to the present invention is small in flow channel area. For this reason, the period of time from when the mobile phase is introduced into the mixer to when the mobile phase is discharged is short, and the time necessary to perform a one-time analysis is short. Furthermore, in a case of the analysis using the gradient elution method, the change in the concentration of the mobile phase, closer to an ideal, may be generated. Furthermore, the mixer disclosed according to the present invention has a period in which the performance of decreasing the concentration non-uniformity in the flow direction of the mobile phase is at the maximum. Since the shorter the period is, the smaller the volume of the flow channel may be, the effect resulting from the decrease in the flow channel volume may be accomplished at the maximum by a system of the liquid chromatograph that drives the liquid sending pump in such a manner as to minimize the period of the concentration non-uniformity.

Furthermore, in the mixer disclosed according to the present invention, the area of the substrate in which the flow channel unit is formed may be decreased by properly arranging the flow channel on the substrate. For this reason, with a comparatively simple configuration that seals a hydraulic pressure, with the substrate being pressed by the housing, the surface pressure added to the substrate may be increased and the higher hydraulic pressure may be sealed. This means that the application to a high pressure liquid sending pump is possible. Furthermore, because the external shape of the housing may also be decreased by decreasing the area of the substrate on which the flow channel unit is formed, a degree of freedom in an arrangement of the components in the liquid chromatograph may be increased.

REFERENCE SIGNS LIST 1, 101, 102, 103 flow channel unit
2 introduction channel
3 branch portion
4 first branched flow channel
5 second branched flow channel
6 junction portion
7 discharge channel
11, 24 mixer
14 flow channel substrate
15 mixer using multiple flow channel substrates
22, 2201, 2202 liquid sending pump
23 junction connector
25 auto-sampler
26 separation column
27 detector
28 pipe
29 controller
30 wiring
31 switch valve
1001 multi-stage flow channel unit
2101, 2102 eluent

The invention claimed is:

1. A liquid mixing device comprising:
a plurality of flow channel units, each comprising:
an introduction channel through which a liquid is introduced;
a branch portion joined to a downstream end of the introduction channel;
a first branched flow channel and a second branched flow channel each extending from the branch portion, the first and second branched flow channels defining a time difference for the liquid to flow through the first branched flow channel relative the second branched flow channel;
a junction portion joining the first and second branched flow channels at an end opposite the branch portion; and
a discharge channel disposed at a downstream end of the junction portion,
wherein the discharge channel of a first flow channel unit of the plurality of flow channel units is joined to the introduction channel of a second flow channel unit of the plurality of flow channel units, the time difference of the first flow channel unit being different than the time difference of the second flow channel unit.

2. The liquid mixing device according to claim 1, wherein each of the plurality of flow channel units is formed on a substrate, substrate of each of the plurality of flow channel units overlapping to allow the liquid to flow through each of the plurality of flow channel units.

3. The liquid mixing device according to claim 1, wherein the plurality of flow channel units are formed on an upper surface and a lower surface of a substrate.

4. The liquid mixing device according to claim 1, wherein the plurality of flow channel units are formed on a single substrate.

5. A liquid mixing device comprising:
a plurality of flow channel units, each comprising:
an introduction channel through which a liquid is introduced;
a branch portion joined to a downstream end of the introduction channel;
a first branched flow channel and a second branched flow channel each extending from the branch portion, the first and second branched flow channels each having a shape and an internal structure defining a time difference for the liquid to flow through the first branched flow channel relative the second branched flow channel based on a period of a concentration non-uniformity in a flow direction resulting from a liquid sending device sending the liquid to the introduction channel;
a junction portion joining the first and second branched flow channels at an end opposite the branch portion; and
a discharge channel disposed at a downstream end of the junction portion,
wherein the discharge channel of a first flow channel unit of the plurality of flow channel units is joined to the introduction channel of a second flow channel unit of the plurality of flow channel units, the time difference of the first flow channel unit being different than the time difference of the second flow channel unit.

6. A liquid chromatograph comprising:
one or more liquid sending devices to send one or more liquids;
a liquid mixing device to mix the one or more liquids, the liquid mixing device comprising:
a plurality of flow channel units, each comprising:
an introduction channel through which a liquid is introduced;
a branch portion joined to a downstream end of the introduction channel;
a first branched flow channel and a second branched flow channel each extending from the branch portion, the first and second branched flow channels defining a time difference for the liquid to flow through the first branched flow channel relative the second branched flow channel;
a junction portion joining the first and second branched flow channels at an end opposite the branch portion; and
a discharge channel disposed at a downstream end of the junction portion,
wherein the discharge channel of a first flow channel unit of the plurality of flow channel units is joined to the introduction channel of a second flow channel unit of the plurality of flow channel units, the time difference of the first flow channel unit being different than the time difference of the second flow channel unit;
an auto-sampler to introduce a specimen into the one or more liquids sent by the one or more liquid sending pumps;
a separation column to separate the one or more liquids into which the specimen is introduced by the auto-sampler;
a detector to detect a component of the specimen in the one or more liquids sent from the separation column;
a pipe to connect the liquid sending pump, the liquid mixing device, the auto-sampler, the separation column, and the detector to one another to allow the liquid to flow; and
a controller to control the liquid sending pump, the auto-sampler, and the detector.

7. The liquid chromatograph according to claim 6, wherein a drive period of the one or more liquid sending devices is determined according to the time difference of each of the plurality of flow channel units in the liquid mixing device.

8. The liquid chromatograph according to claim 6, further comprising: a switch valve that switches an amount of the one or more liquids.

9. The liquid chromatograph according to claim 8, wherein a switch period of the switch valve is determined according to the time difference of each of the plurality of flow channel units in the liquid mixing device.

* * * * *